United States Patent [19]

Mersch

[11] Patent Number: 4,936,679
[45] Date of Patent: Jun. 26, 1990

[54] OPTICAL FIBER TRANSDUCER DRIVING AND MEASURING CIRCUIT AND METHOD FOR USING SAME

[75] Inventor: Steven H. Mersch, Dayton, Ohio

[73] Assignee: Becton, Dickinson and Company, Franklin Lakes, N.J.

[21] Appl. No.: 797,299

[22] Filed: Nov. 12, 1985

[51] Int. Cl.$^5$ .............................................. G01N 33/41
[52] U.S. Cl. ........................................ 356/41; 128/364
[58] Field of Search ................. 356/41, 432, 433, 434; 250/373; 364/416; 128/634, 637

[56] References Cited

U.S. PATENT DOCUMENTS

| | | | |
|---|---|---|---|
| 3,847,483 | 11/1974 | Shaw et al. | 356/41 |
| 3,892,468 | 7/1975 | Duguay | 250/227 |
| 4,050,450 | 9/1972 | Polanyi et al. | 356/41 |
| 4,054,366 | 10/1977 | Barnoski et al. | 350/96.15 |
| 4,266,554 | 5/1981 | Hamaguri | 356/41 |
| 4,476,870 | 10/1984 | Peterson et al. | 356/41 |
| 4,487,206 | 12/1984 | Aagard | 128/634 |
| 4,622,974 | 11/1986 | Coleman et al. | 128/634 |

FOREIGN PATENT DOCUMENTS 47734 4/1981 Japan .................................. 356/437

OTHER PUBLICATIONS

Merrick et al., "Continuous, Non-Invasive Measurements of Arterial Blood Levels", *Hewlett-Packard Journal*, vol. 28, No. 2 (Oct. 1976), pp. 2–9.

Querry et al., "Split Pulse Laser Method for Measuring Attenuation Coefficients of Transparent Liquids", *Applied Optics*, vol. 17, No. 22 (15 Nov. 1978), pp. 3587–3592.

*Primary Examiner*—Richard A. Rosenberger
*Attorney, Agent, or Firm*—Robert P. Grindle

[57] ABSTRACT

Disclosed in an optical fiber transducer system with energy generating means for transmitting pulsing energy at various frequencies to bidirectional couplers for each frequency. The couplers record the intensity and further transmit the pulsing energy to a wavelength multiplexer/demultiplexer. The wavelength multiplexer/demultiplexer combines the plurality of energy supply means into a single output for an optic fiber which includes an optical delay sufficient to time separate the pulsing waves of energy. Reflected energy is transmitted back through the same wavelength multiplexer/demultiplexer, bidirectional coupler so that the recorded intensity of transmission and reflectance are comparable without system influence. A method is also shown for use of an optical fiber system including the components set forth and the system requires the generation and combination of the various frequencies of energy in a multiplexer/demultiplexer, the delay for time separation and the detection in a bidirectional coupler of transmitted and reflected energy.

11 Claims, 2 Drawing Sheets

OPTICAL FIBER TRANSDUCER DRIVING AND MEASURING CIRCUIT AND METHOD FOR USING SAME

BACKGROUND OF THE INVENTION

1. Field

This invention relates to a catheter instrument which measures physiological parameters of blood while same is located inside the human blood stream. The technique is made feasible by means of an elongated optical fiber transducer which in a well-known manner transmits light into the blood and carries the reflectance of that light back to the instrument from which it was transmitted.

2. State of the Art:

Devices for performing such measurements are known as oximeters and same are disclosed in the Shaw U.S. Pat. Nos. 3,638,640; 3,847,483; 4,114,604; 4,295,470; 4,416,285; 4,322,164 and Vurek U.S. Pat. No. 3,799,672 and Heinenmann U.S. Pat. No. 4,447,150 among others. These patents deal primarily with measurement of oxygen saturation in the blood. Oxygen saturation is the relative amount of oxygenated hemoglobin in all of the hemoglobin of the blood stream. Hemoglobin is packed in bioconcave disks of shaped red blood cells having a diameter of approximately 10 micrometers. Whole blood has a density of about 5 million red blood cells per cubic millimeter. Since the red blood cells both scatter and transmit the incident radiant energy, the differential absorption by oxygenated and non-oxygenated hemoglobin of the radiant energy transmitted through the blood gives a basis for oxygen saturation measurement. It can be seen that an optical fiber catheter transmits light to the position of interest within the flowing blood stream and a return fiber optic light guide conducts the reflected light from the blood stream back to a photo detector.

When blood in a human body is the test medium, there are a number of problems with measuring oxygen saturation which arise. These problems are fully detailed in the aforesaid patents. Briefly, however, the transducer itself introduces errors due to the two fiber optics connected to the detector system used to measure the light transmitted and reflected. In addition to this, the blood flow is pulsatile and as such the conditions to be measured are constantly fluctuating. Previous mathematical compensations for changes in hematocrit blood flow velocity, pH, PC02, and the like introduce errors into the oxygen saturation measurement. Similarly, variations in osmolarity and in transmissivity of the two optical fibers is also present and can result in influencing the ultimate measurement.

Several wavelengths are necessary in order to make measurement. That is to say that, light must be transmitted to the oxygenated hemoglobin at a minimum of two different wavelengths and the reflectance of those wavelengths when compared with the light transmitted gives the oxygen saturation in accordance with the following equation:

$$OS = \frac{A_0 + A_1 I_1 + A_2 I_2}{B_0 + B_1 I_1 + B_2 I_2}$$

As explained in the Shaw U.S. Pat. No. 4,114,604, oxygen saturation is a function of the ratios of light intensity measurement of the several wavelengths.

SUMMARY OF THE INVENTION

The present invention is an advancement in the art of blood oxygen saturation measuring instruments. In particular, it is involved with the arrangement of a single transducer fiber optic element and the related circuitry. The system herein recognizes that transmitting and receiving an optical signal must be accurate enough to give repeatable readings of blood oxygenation. Problems with non-uniform attenuation affects for the various wavelengths, variations in the output from the light sources and weak optical return signals have in the past caused considerable difficulty.

The preferred system has disposable and non-disposable sections. The disposable section is a large core approximately 200 micrometers, single glass fiber with a suitable connector. The distal end of the fiber need not be polished to any stringent specification. The multiple wavelengths of light are transmitted and received through that fiber optic element. This is enabled by the heart of the system which is a fiber optic bi-directional coupler for each wavelength and an optical fiber wavelength multiplexer/demultiplexer for combining all of the wavelengths. To obtain instantaneous measurements, the system operates by using a series of pulsed signals. This eliminates problems with changes as an instantaneous measurement is obtained from each pulse.

For a given pulse, the source of the timing is a computer or similar electronic device which sends a signal to trigger the transmitted light source through the bi-directional coupler. This is done simultaneously for the several wavelengths or color frequencies. A 100 nanosecond light signal is generated and by means of the cross-talk in the bidirectional coupler a detector measures the relative intensity of the energy to be transmitted, and that measurement is stored in sample and hold circuitry. Since there are several color frequencies, the generated pulses to be transmitted from each light source are combined into a single glass fiber by the wavelength multiplexer/demultiplexer from which they travel through a fiber optic delay coil of about 25 meters to thereby separate the timing between the transmitted and reflected pulses.

These signals are then connected and transmitted through the disposable section of the system. That is, the fiber optic, in a catheter in a living human being. The pulsed light reflected from the blood travels the same path but in reverse to the same detector which measures the intensity of the original burst of energy. The reflected signal intensity from the detector is normalized by dividing same by the originally pulsed signal intensity. Since the same detector is used for measuring intensity of transmission and reflectance, and the same fiber optic is used for the various wavelengths, no error or differences are introduced by these components. Moreover, since the electronics perform the calculation of oxygen sensor saturation on the ratio of transmitted reflected intensities, variations in the original intensity of the transmitted signal are automatically taken into account.

There are numerous advantages to this arrangement. Because there is only a single fiber optic, a larger fiber can be used but its overall size will be smaller than that used in a two or three fiber optic system, and the use of a single fiber enhances a strong return signal. Moreover, the electronics necessary for driving and measuring the transmission and reflectance can be compact. It can be seen that since only one fiber optic is used, bending losses, coupling losses, fiber defects, and the like are the same for each of the wavelengths transmitted and reflected through that single fiber. The only material that treats the various wavelengths differently is the test medium or blood. In the algorithm used for calculating oxygen saturation, the percent reflected signals of each wavelength are divided into each other. In that calculation, the common errors are cancelled. However, wavelength sensitivity affects of the blood or test medium are not cancelled. For all the foregoing reasons, the assembly of the disposable or fiber optic portion becomes much less critical, and once the main electronic circuitry is calibrated, it should not be necessary to recalibrate for each disposable used. That is to say that, it is merely the differences in the reflection of energy from the test medium which is of interest and not the myriad of other factors which normally affect these types of instruments.

The pulse technique used for making the measurement assures precision by averaging a large number of readings and normalizing the signal to cancel the affects of non-consistent source intensities By use of a glass fiber attenuation losses in the 25 meter delay coil are minimized.

DETAILED DESCRIPTION OF THE DRAWINGS

While a specific preferred embodiment for measurement of oxygen saturation in blood is shown and disclosed herein, those skilled in the art will no doubt appreciate that depending upon what is sought to be measured in a particular test medium the wavelength selected, the number of wavelengths used, the particular construction of the fiber optic, the kind of analysis circuitry applied and the like can be varied. Therefore, the description here is by way of example in connection with one test medium and one factor to be measured therein; and by no means should the details of the preferred construction be considered as necessary for practicing the invention.

Figure 1:
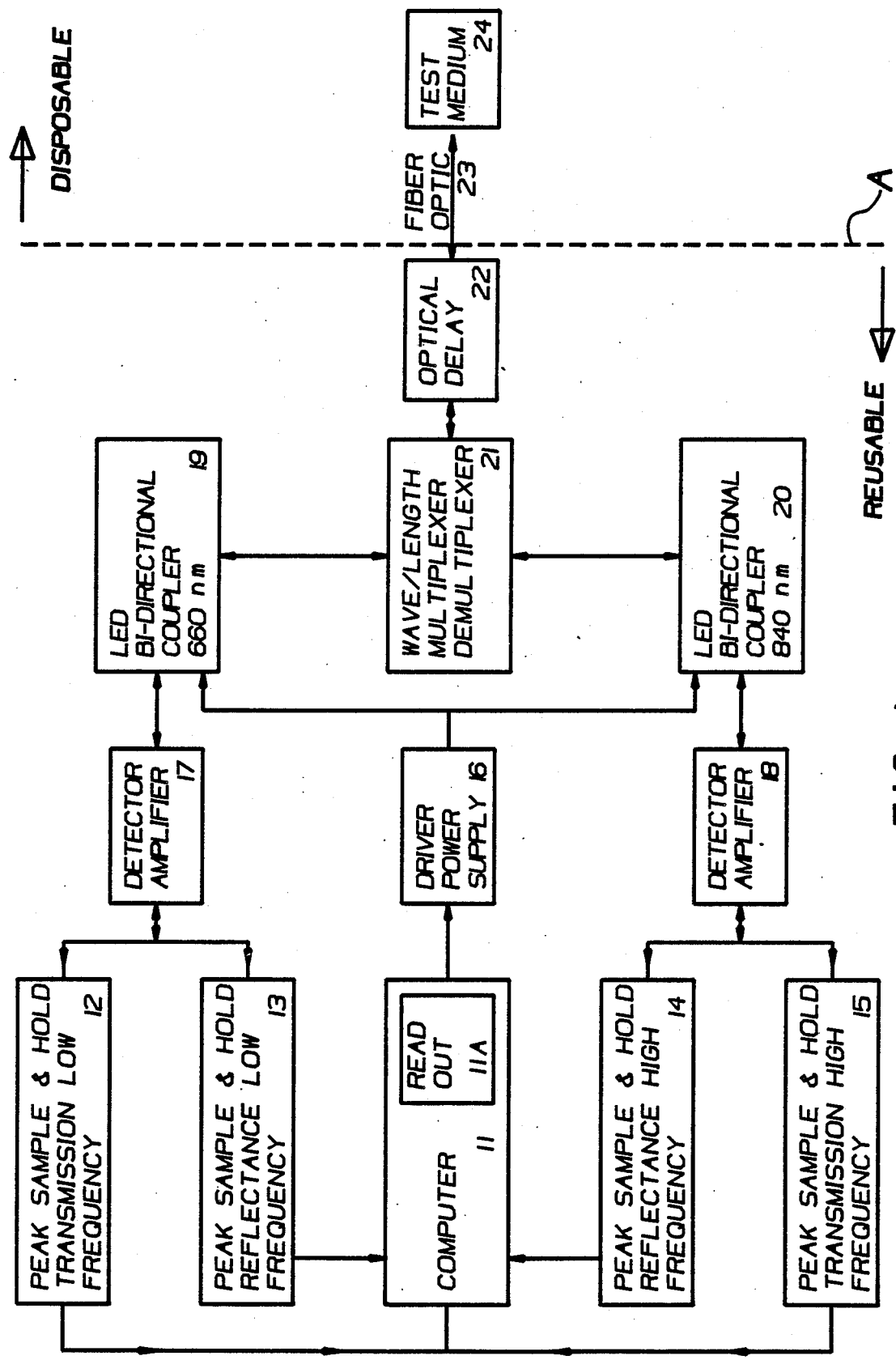
FIG. 1 is a block diagram showing the relative relationship of the electronic components of an oxygen saturation sensor system.

FIG. 1 is a block diagram showing the electronic circuitry for the system with all of the connections between the various components. In addition to which the reusable and disposable portions of the system are separated by vertical dotted line "A" provided between the portions of the system. In explaining the electronic circuitry of the reusable portion of the system various components thereof will first be outlined and their relative functions explained. Thereafter, the connections between those functioning components will be explained in detail.

The timing for the system is established by the computer 11 which sets the frequency for the pulsed signals and all of the calculation for the received data. The computer 11 includes a readout 11a which could be in the form of a visible screen or a printer or both but is not shown or described herein as skilled artisans will know how same can be applied. It will be noted that the computer 11 is connected to peak sample and hold circuits 12, 13, 14 and 15 for several wavelength frequencies (only two are shown in FIG. 1). One is designated as low and the other is designated as high, it should be appreciated that as many peak sample and hold circuits could, as are necessary, be used for the number of wavelengths required. There are peak sample and hold circuits 12, 13, 14, 15, etc. for transmission and reflectance for each color frequency or wavelength of energy. A trigger signal of the required frequency is sent from the computer 11 to a driver power supply 16 which generates timed bursts of power of the given frequency to an LED source. Detector amplifiers 17 or 18 receive a fixed percentage of the energy emitted by the LED source. The relative level of energy in the original burst from the LED is, therefore, measured and sent to its peak sample and hold 12, 13, 14, or 15 for storage. The detector 17 or 18 also includes an amplifier which increases the signal. For each of the color frequencies used, there is a detector amplifier 17 or 18.

A preferred fiber-optic chassis is made by the Kaptron Corporation of Palo Alto, Calif. and is described as FOMD04. This chassis contains bi-directional couplers 19, 20, etc. and wavelength multiplexer/demultiplexer 21. While the detector amplifier 17 or 18 and the bi-directional coupler 19 or 20 are shown as independent components in the block diagram of FIG. 1, it should be appreciated by skilled artisans that devices are available and combine the functions of detector and bi-directional coupler. However, for clarity in the description and simplification of the understanding of the various functions of the system, the block diagram shows these functions separately. In addition to that, the LED light-emitting diode is mentioned as a separate part connected to the driver power supply 16. In the particular Model FOMD-04, a bidirectional coupler of the Kaptron Corporation, there is an LED emitter and a beam divider such that the driver power supply will, in accordance with the computer input, set the color frequency for powering the light emitting diode located in the bi-directional coupler 19 or 20. By means of a beam divider, the burst of energy will be supplied not only outwardly toward the fiber optic in the catheter, but also inwardly toward the detector whereby the intensity of a given emission of the light emitting diode will be measured concurrently with its transmission.

In accordance with the frequency established by the computer, the bi-directional coupler 19 or 20 will put out a burst of energy at 660 nm or 840 nm when same are in an oxygen saturation measuring circuit. The bi-directional couplers 19 and 20 are connected to a wavelength division multiplexer/demultiplexer 21 as shown in FIG. 1. This multiplexer/deplexer is used to combine light signals at two distinct color frequencies or wavelengths into an output to be transmitted by a single fiber or in the reverse to split two signals on the same fiber into two separate signals or outputs depending on which direction the signal is transmitted through the wavelength division multiplexer/demultiplexer 21. It is an all-passive arrangement, and therefore, is highly reliable. Normally these devices are used for dual channel video transmission or telecom circuit conversation, i.e., four wire circuits to a single fiber. Here, however, the wavelength multiplexer/demultiplexer 21 is used to combine the color frequencies 660 nm and 840 nm so that same may be sent through a single fiber to the test medium. In the particular circumstance described herein, the fiber passes through a catheter and the test medium is human blood inside a living human. Reflectance of the energy is received by the wavelength division multiplexer/demultiplexer 21 and split into the two color frequencies whereby same are sent back to the detectors via the bi-directional couplers 19 and 20 so that the intensity of the reflected signal can be measured. Wavelength division multiplexers/demultiplexers are available for more than two inputs.

The output of the wavelength division multiplexer/demultiplexer 21 is connected to a fiber optic optical delay 22. Optical delay 22 is, therefore, located between the catheter 23 and the wavelength division multiplexer/demultiplexer 21. The optical delay 22 is nothing more than a device which provides increased distance approximately 25 meters through which the optical signal must travel. That is to say that, the signal that has been combined by the wavelength division multiplexer/demultiplexer 21 is carried along a lengthened path whereby the time necessary for it to travel through the optical delay 22 is increased. The purpose of this time delay is to give enough time (as will be described in connection with FIG. 2) to allow the electronics controlling the sample and hold circuits sufficient time spacing between signals to consider each burst of energy for each of the color frequencies. Beyond the optical delay 22 is the disposable portion of the optical fiber transducer system for measuring a parameter of a test medium such as blood.

In the particular circumstances of the preferred embodiment, there is a single fiber optic element about 200 um in diameter disposed in catheter 23. This fiber optic element is obtained from Ensign-Bickford Optics Company and is about four feet long. It is radiation resistant and clad in hard polymer in order to help the transmission of energy therethrough. The length of the optical delay 22 is approximately 25 meters, and when combined with the length of the fiber optic element in catheter catheter 23 the signal is delayed sufficiently to allow the measuring of both color frequencies, i.e., the reflectance and transmission without mixing either with the other. The fiber optic and catheter 23 in the preferred system are disposable. The combination of the two have an outer diameter of approximately 0.1 inches and are designed for insertion into the vascular system of the human being.

In operation, light transmitted through the fiber optic 23 to the test medium 24 is influenced by the test medium such that reflected light returning up the fiber optic element in catheter 23 through the delay 22 and into the wavelength division multiplexer/demultiplexer 21 is influenced as a function of the parameter of the test medium to be measured. In the particular circumstance of oxygen saturation in blood, and in accordance with the description in the background and summary herein the reflectance is a measure of the oxygen saturation of the hematocrit. In the wavelength division multiplexer/demultiplexer 21, the color frequencies of 660 nm and 840 nm are split or divided and sent back to their respective bidirectional couplers 19 or 20 wherein the light passing therethrough remains distinct from the light being transmitted therethrough, and is thereby transmitted to the detector 17 or 18 respectively where the intensity of the reflected light from the test medium is measured. Thereafter, the signal is transmitted to the peak sample and hold circuits for reflected light 13 or 14 to be held until such time as the computer 11 is ready to receive that information and use same to calculate the difference between specific bursts of transmitted light and reflected light. A level of saturated oxygen in the blood or any other parameter in any other test medium can be obtained in that way and that information will then be displayed on the readout 11a of the computer 11.

Figure 2:
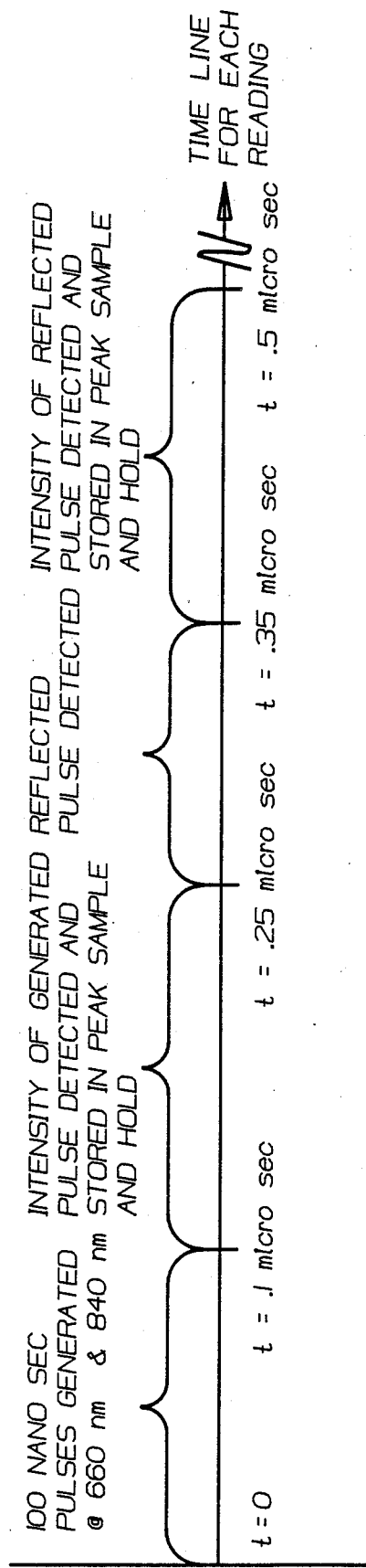
FIG. 2 is a time line diagram showing the relative spacing within a period of time of the events necessary to take one reading. Because of the high speed of this system, 1,000 readings can be taken per second and averaged thereby updating the output every second.

Turning now to FIG. 2 which is a time diagram showing the relative relationship between the events of the system described in connection with the block diagram of FIG. 1, time is shown on the abscissa and the total time shown for one cycle of the sytem is 0.5 microseconds. In particular, the first 0.1 microsecond is allocated for the generation of pulses at 660 nm and 840 nm. The next 0.15 microseconds is used to measure the relative intensity of the generated pulses whereby same can be detected in the detector amplifier 17 or 18 and stored in the generated transmission peak sample and hold 12 or 15. During the next 0.1 microseconds the reflected pulse is detected and the subsequent 0.15 microseconds is used for measurement of the intensity of the reflected pulses in the detector amplifier 17 and 18 and storage of same in the peak sample and hold circuits 13 and 14. It can be seen then that the entire time for a given cycle is 0.5 microseconds and same is sufficiently long because of the optical delay 22 which allows time for the switching of the sample and hold circuits.

Because the wavelength division multiplexer/demultiplexer can be expanded to handle multiple (up to 20) color frequencies, the technique described here can be likewise expanded to measure multiple parameters in the test medium. In the example of measuring blood oxygenation, a third wavelength at 940 nm can be added, and measurement of cardiac output can be performed using indocyanide green injection as described in the literature.

While a particular system for a parameter, oxygen saturation in blood, has been described in detail, it should be appreciated that the basic concept is the combination of the various frequencies into a single output for one fiber optic. This concept permits a more compact system and eliminates the disparities introduced by several fiber optics. In addition to this, the importance of using the same detector for measuring transmitted and reflected intensity eliminates any error introduced by having more than one detector. The optical delay makes this possible. Finally, the high pulse rate of the system insures high precision. Skilled artisans will no doubt appreciate that other components could be used with the aforesaid concepts to achieve the results desired. With this in mind, the claims which follow are designed to cover the broader concept suggested as well as the particularly preferred embodiment.

What is claimed:

1. An optical fiber transducer system utilizing a single fiber optic for transmitting energy for measurement of a parameter of a test medium and for receiving the reflected energy from said medium for comparison; characterized by
   (a) a power supply;
   (b) a first energy source connected to said power supply for emitting bursts of energy at a first predetermined color frequency;
   (c) a second energy source connected to said power supply for emitting bursts of energy at a second predetermined color frequency;
   (d) a wavelength division multiplexer, demultiplexer connected to said first and second energy sources for receiving said bursts of energy;

(e) said multiplexer/demultiplexer for maintaining the discrete color frequencies of said received first and second bursts of energy while combining them;

(f) said multiplexer/demultiplexer further transmitting said first and second bursts of energy while separating the reflected energy thereof into individual channels of each color frequency upon the return thereof;

(g) a single fiber optic connected to said multiplexer/demultiplexer for transmitting said bursts of energy at said first and second color frequencies to and into said test medium from said multiplexer/demultiplexer and for carrying the reflected energy thereof directly and only from said test medium to said multiplexer/demultiplexer;

(h) optical delay means connected to said single fiber optic for extending the distance of said transmitted and reflected energy of said combined first and second color frequencies for permitting time separation of said transmitted and reflected energy for the discrete measurement thereof;

(i) a detector connected to each of said first and second energy sources;

(j) each said detector for measuring and storing the level of energy for its specific predetermined color frequency during the transmission thereof, and for subsequently measuring the reflected energy thereof for comparing the degree of transmitted and reflected energy; and (k) computer means for establishing the timing of said bursts of energy, and for receiving said detected level of transmitted and reflected energy for each color frequency for establishing the percent of reflected energy over said transmitted energy.

2. The optical fiber transducer system of claim 1 wherein said first and second color frequencies are about 660 nm and 840 nm, respectively, the test medium is blood in vivo, and the measured parameter is oxygen saturation.

3. The optical fiber transducer system of claim 1 wherein said fiber optic is in series with said optical delay means and the combination of same is long enough to allow the time necessary for said computer means to determine the transmitted and reflected energy by time delay separation between the two resulting from the increased distance of travel necessary for the transmitted and reflected energy pulses.

4. The optical fiber transducer system of claim 1 wherein said computer means triggers said power supply to establish said bursts of energy for the transmitted wave and compares that energy with the energy received from the reflectance of that wave.

5. A method for measuring a parameter of a test medium utilizing an optical fiber transducer system by comparing transmitted energy to and into said medium with the energy reflected solely from said test medium; the steps which comprise (a) triggering the signal for a power supply in accordance with at least two color frequencies of timed pulses;

(b) generating a pulsing supply of energy at predetermined color frequencies in response to said triggering step;

(c) emitting bursts of light energy at said predetermined color frequencies in response to said pulsing power supply;

(d) detecting in a first detecting step said bursts of light energy from said emitting step as they are transmitted;

(e) storing information from said first detecting step;

(f) multiplexing said predetermined transmitted bursts of light energy at said predetermined color frequencies from said emitting step into a common output;

(g) imposing a delay on said common transmitted output of distinct color frequencies from said multiplexing step;

(h) sending said delayed common output along a single fiber optic to and into a test medium;

(i) receiving said common output of distinct color frequencies reflected directly and only from said test medium through said same fiber optic;

(j) detecting in a second detecting step, and storing, said reflected color frequencies with the same detector from said first detecting step; and (k) forwarding the detected information from said first and second detecting step to a computer so that the difference can be calculated for each color frequency.

6. An optical fiber transducer system utilizing a single fiber optic for transmitting energy for measurement of a parameter of a test medium and for receiving the reflected energy directly and only from said medium for comparison; characterized by (a) a power supply;

(b) at least two energy sources connected to said power supply for emitting bursts of energy simultaneously at different predetermined color frequencies for each said energy source;

(c) a wavelength division multiplexer/demultiplexer connected to said at least two energy sources for receiving said bursts of energy;

(d) said multiplexer/demultiplexer for maintaining the discrete color frequencies of said received bursts of energy while combining them;

(e) said multiplexer/demultiplexer further transmitting said received bursts of energy while separating the reflected energy thereof into two or more individual channels upon the return thereof with one channel for each color frequency;

(f) optical delay means connected to said multiplexer/demulitplexer for extending the distance of said transmitted and reflected energy of said two or more bursts of energy for permitting time separation of adjacent bursts of transmitted and reflected energy at specific color frequencies for the discrete measurement thereof;

(g) a single fiber optic element connected to said optical delay means for receiving said delayed transmitted bursts of energy and transmitting them to and into said test medium, and for receiving the reflected energy of said bursts of energy directly and only from said test medium;

(h) a plurality of detectors with one each connected to each of said energy sources;

(i) each said detector for measuring and storing the level of energy for its specific predetermined color frequency during the transmission thereof, and for subsequently measuring the reflected energy thereof for comparing the degree of transmitted and reflected energy; and (j) computer means for establishing the timing of said bursts of energy, and for receiving said detected level of transmitted and reflected energy for each color frequency for establishing the percent of reflected energy over said transmitted energy.

7. The optical fiber transducer system of claim 6 wherein said fiber optic is in series with said optical delay means and the combination of same is long enough to allow the time necessary for said computer means to determine the transmitted and reflected energy by time delay separation between the transmitted and reflected energy of a single burst as a result of the increased distance of travel imposed by said optical delay means.

8. The optical fiber transducer system of claim 6 wherein said computer means triggers said power supply to establish said bursts of energy for the transmitted wave and compares that energy with the energy received from the reflectance of that wave resulting from that same burst.

9. The optical fiber transducer system of claim 6, further characterized by
 (a) said single fiber optic element is disposable.

10. The optical fiber transducer system of claim 6, further characterized by
 (a) a bi-directional coupler connected to each said energy source for detecting the intensity of said emitted burst of energy therefrom, and further transmitting said burst of energy to said multiplexer/demultiplexer.

11. The optical fiber transducer system of claim 6, further characterized by
 (a) each said bi-directional coupler detects reflected pulsating energy waves.

* * * * *